United States Patent [19]

Okahata et al.

[11] Patent Number: 5,081,048

[45] Date of Patent: Jan. 14, 1992

[54] AGENT FOR THE DETERMINATION OF ANTIGEN OR ANTIBODY, AND A DEVICE AND MEASURING METHOD RELATED THERETO

[75] Inventors: Yoshio Okahata, Kawasaki; Naofumi Takahashi, Sagamihara; Takuro Sada, Yokohama, all of Japan

[73] Assignee: The Nisshin Oil Mills, Ltd., Tokyo, Japan

[21] Appl. No.: 321,799

[22] Filed: Mar. 10, 1989

[30] Foreign Application Priority Data

Mar. 11, 1988 [JP] Japan ................... 63-57628

[51] Int. Cl.$^5$ .......................................... G01N 33/547
[52] U.S. Cl. ..................... 436/532; 436/528; 436/530; 436/533; 436/800; 436/805; 436/807; 436/810; 436/823
[58] Field of Search ............... 436/518, 531, 532, 528, 436/530, 533, 800, 805, 807, 810, 823

[56] References Cited

U.S. PATENT DOCUMENTS

| | | | |
|---|---|---|---|
| 4,267,234 | 5/1981 | Rembaum | 428/407 |
| 4,278,651 | 7/1981 | Hales | 436/532 |
| 4,615,985 | 10/1986 | Deutsch et al. | 436/532 |
| 4,695,554 | 9/1987 | O'Connell et al. | 436/528 |

FOREIGN PATENT DOCUMENTS 144084 6/1985 European Pat. Off. ............ 436/528

OTHER PUBLICATIONS

J. Chem. Soc. Perkin Trans, II 1987, pp. 1317–1319, Okahata et al., "Functional Capsule Membranes, part 29."

Macromolecules 1987, 20, pp. 15–21, Okahata et al., "Functional Capsule Membranes, 26, Permeability Control of Polymer-Grafted Capsule Membranes Responding to Ambient pH Changes."

Primary Examiner—Mary E. Ceperley
Attorney, Agent, or Firm—Wegner, Cantor, Mueller & Player

[57] ABSTRACT

An agent or device for the determination of antigen or antibody comprising capsules of a water-insoluble, dye-permeable polymer or a liquor-pool covered by said polymer, an antien, antibody or hapten immobilized on the surface of said polymer, and a dye solution enclosed or held in said capsules or liquor-pool, and a method for determining antigen or antibody using said agent or device, which can be conveniently used for the serodiagnosis of various diseases.

21 Claims, No Drawings

AGENT FOR THE DETERMINATION OF ANTIGEN OR ANTIBODY, AND A DEVICE AND MEASURING METHOD RELATED THERETO

BACKGROUND OF THE INVENTION

1. Field of the Invention

The present invention relates to an agent or device for the determination of antigen or antibody, and a method for determining antigen or antibody using the agent or the device.

2. Description of the Prior Art

In the field of clinical analysis, it is known to detect an antibody or antigen in a blood or serum sample with a high sensitivity, by utilizing the agglutination reaction of an antigen, antibody or hapten immobilized to a carrier with the corresponding antibody or antigen, and so the detection by such agglutination reaction is widely adopted for the serodiagnosis of various diseases. As the carriers for the agglutination reaction, synthetic carriers such as a polystyrene latex, etc. and bio-carriers using red blood cells, bacterial cells, etc. are used (U.S. Pat. No. 3,088,875).

Generally, the synthetic carriers are chemically stable and have merits that they themselves have no antigenicity, while they have demerits that antigens, antibodies or haptens are not easily coupled to them. Further, they involve problems such as uniformity in particle diameter, non-specific agglutination, and the like.

On the other hand, the bio-carriers have defects such as low stability, low sensitivity in detection due to their own antigenicity, and the like, although they have merits such as stability in particle diameter.

A purpose of the present invention resides in providing novel agent and novel device which firmly immobilize antigens, antibodies or haptens and are capable of detecting antibodies or antigens in a sample with a high sensitivity, as a clinical reagent or material.

Another purpose of the present invention resides in providing a method for determining antigen or antibody using the above agent or device.

SUMMARY OF THE INVENTION

The present invention provides an agent for the determination of antigen or antibody which comprises a water-insoluble, dye-permeable polymer capsule having an average particle diameter of 0.1-5 mm, an antigen, antibody or hapten immobilized onto the surface of said polymer capsule through a polymer chain grafted to said capsule, and a dye solution enclosed in said capsule; and a device for the determination of antigen or antibody, which comprises liquid-pool composed, at least partially, of a water-insoluble, dye-permeable polymer film, an antigen, antibody or hapten immobilized onto the outer surface of said polymer film through a polymer chain grafted to said capsule, and a dye solution held in said liquor-pool.

Further, the present invention provides a method for determining antigen or antibody which comprises subjecting the agent or device as mentioned above into contact with a sample liquor to make the dye to release into the sample liquor, and determining the antigen or antibody in the sample liquor by detecting the change in releasing rate or released amount of the dye, which may be caused with the proceeding of an antigen-antibody reaction of the immobilized antigen, antibody or hapten, on the basis of the absorbance or fluorescence intensity.

According to the present invention, an antigen or antibody in a sample can be detected with a high sensitivity, by determining the change in releasing rate or released amount of the dye.

DETAILED DESCRIPTION OF THE PREFERRED EMBODIMENT

The polymer in the water-insoluble, dye-permeable polymer capsule is, for example, so-called vinyl polymers such as low density polyethylene, high density polyethylene, straight chain low density polyethylene, ethylene/vinyl acetate copolymer, polypropylene, propylene copolymer, polyvinyl chloride, polyvinylidene chloride, polystyrene, polyacrylonitrile, polytetrafluoroethylene, etc., so-called polycondensation products such as polyethylene terephthalate, polyethylene isophthalate, nylon 6, nylon 66, nylon 12, etc., polyaddition products such as polyurethane, polysulfone, etc., natural high molecular materials such as cellulose, wool, etc., or the like. Among these polymers, nylons are preferably used.

The polymer capsules in the present invention may be prepared using a monomer for the above polymers, according to a process for preparing micro-capsules which is known in the art. For example, when a nylon is used, a monomer is added dropwise to the solution containing the copolymerizable monomer and a catalyst to cause the polycondensation on the surface of the monomer drops, the drops are taken out from the solution as a capsule outer wall having a desired thickness is formed, and then the unpolymerized monomer remaining inside is removed by it with a solvent or the like, to obtain nylon capsules. The capsule is suitably one having an average particle diameter of 0.1-5 mm.

The polymer film of the present invention may be prepared from a monomer for the above polymer, according to a known process for forming films. The polymer film is suitably one having a thickness of 1-10 $\mu$m, in view of the strength and the dye-permeability. The polymer film may be in the form supported on a suitable porous or mesh substrate. For example, it may be an uneven film formed at the apertures of a porous polyester or polyvinylchloride resin substrate.

Usually, the polymer chain grafted to the capsule or film has a functional group to immobilize an antigen, antibody or hapten. Examples of the functional groups are amino, sulfonate, carboxyl or hydroxy group. There are various methods for introducing such graft polymer chain into the capsule or film. For example, when a nylon is used as the polymer material, a double bond moiety is firstly introduced to the nylon by a graft polymerization of a small amount of divinyl monomer using a cerium salt as catalyst and then a vinyl monomer having amino group, sulfonate group, carboxyl group or hydroxyl group is graft polymerized using potassium persulfate as catalyst, to form the graft polymer chain.

It is also possible to effect a graft polymerization of a vinyl monomer having a functional group directly onto the capsule or film surface, using a cerium salt as catalyst. As the monomer having a functional group, one having an amino group, such as p-aminomethylstyrene, ethyleneimine, allylamine, etc., is preferably grafted onto the capsule. As the polymerization initiator, ammonium cerium nitrate, potassium persulfate, or the like is used.

The length and the grafting ratio of the resulting polymer chain can be controlled easily by changing the molar ratio of the monomers, and the like. Further, the hydrophilism and the hydrophobism of the capsule or film surface can be controlled by the selection of the monomers.

To the polymer capsule or film having a graft polymer chain thus obtained, an antigen, antibody or hapten is immobilized.

Specific examples of the antigen, antibody or hapten include hormones such as adrenocorticotrophic hormone (ACTH), thyroid-stimulating hormone (TSH), insulin, etc., cancer specific substances such as α-fetoprotein (AFP), carcinoembryonic antigen (CEA), sugar chain antigen CA19-9, etc., serum protein substances such as IgG, fibrin and fibrinogen degradation substance (FDP), antithrombin III (AT III), C-reactive protein (CRP), etc., virus such as hepatitis (HB), AID, adult T cell leukemia (ATL) etc., and rheumatoid factors. Other antigens, antibodies or haptens are also usable.

The immobilization of the antigen, antibody or hapten is effected by a conventional chemical cross linking method corresponding to each of the above-mentioned functional groups. Examples of chemical cross linking methods include method using glutaraldehyde, method using appropriate condensing agent (e.g., Woodward's reagent K (WR-K), N,N-dicyclohexylcarbodiimide, carbonyldiimidazole, and others).

Besides, as the case may be, the antigen, antibody or hapten may be immobilized on the polymer capsule or film by physical absorption, where the polymer chain grafted to the capsule or film does not necessarily possesses the functional group as mentioned above.

The agent of the present invention in the form of the capsule is obtained by allowing the polymer capsule, to which an antigen, antibody or hapten is immobilized, and to enclose a dye solution, especially an aqueous dye solution, therein. The enclosing of a dye solution here can be effected by allowing the above-mentioned immobilized polymer capsule to stand in an aqueous dye solution for a prescribed time period, to introduce the dye into the aqueous phase inside the capsule by dialysis. As the dye here, a hydrophilic dye is used. There is no special limitation for the hydrophilic dye used. It can be, for example, a red dye such as rhodamine, Bordeaux-S, fuchsine, eosine, etc., or a blue dye such as methylene blue, crystal violet, etc. When a higher determination sensitivity is required, it is preferred to use a fluorescent dye such as FITC, TRITC, XITC, carboxyfluorescein, 1-(quinamido-methyl)naphthalene, etc. The introduction of dye may be effected just before the determination as described hereinafter of an antigen or antibody. Suitable concentration of the dye in the solution enclosed is 0.01–100 mM. Especially, it is preferable to adjust the concentration to 0.1–10 mM for carboxyfluorescein or 1-(quinamido-methyl)naphthalene. Such agent of the present invention in the form of capsule may be used in the form of its dispersion in a liquid or in the state as its surface is dry.

The device of the present invention using a immobilized polymer film can be prepared, for example, by applying the immobilized polymer film to one end of a glass or plastic tube having inner diameter of about 0.1–50 mm, with its immobilized surface being situated outside, to compose a liquor-pool, and introducing the above-mentioned dye solution, especially an aqueous dye solution, in the liquor-pool.

Determination of an antigen or antibody with the agent or device of the present invention is effected by subjecting it into contact with a sample liquor such as blood or serum which may contain an antigen or antibody. When the agent in the form of capsule is used, the contact can be performed by adding the capsules themselves or their dispersion in a suitable liquid to the sample liquor and if necessary, agitating the mixture. In the case of a device in the form of the liquor-pool, the contact can be performed by dipping the part where the immobilized polymer film is applied, in the sample liquor for a prescribed time and, if necessary, agitating the liquor.

Under such contact conditions, the dyes in the capsule or in the liquor-pool covered by the film are released into the sample liquor at a prescribed rate, through the micro-apertures or micro-openings of the capsule wall or the film. However, when an antigen-antibody reaction arises by the antigen, antibody or hapten immobilized to the capsule or the film, the corresponding antibody or antigen contained in the sample liquor are coupled to said antigen, antibody or hapten and the micro-apertures or openings of the capsule wall surface or the polymer film surface are narrowed, whereby the rate of the dyes released are reduced. Accordingly, it becomes possible to determine the degree of antigen-antibody reaction and, in turn, the amount of antibody or antigen in a sample liquor, by monitoring the change in releasing rate or released amount of the dye on the basis of the change in the absorbance or fluorescence intensity of the sample liquor. The change in the absorbance or fluorescence intensity can be measured by the conventional spectrophotometer.

The invention is further illustrated by Examples.

EXAMPLE 1

Ethylene glycol dimethacrylate (EDM) was added to 50 ml of tetrahydrofuran (THF) and, into the solution, 8 mg of nylon 12 capsules (2 μm in average diameter) were put and nitrogen gas was introduced. Then, ammonium cerium nitrate as a polymerization initiator was added to the solution and the graft polymerization was effected at room temperature while introducing nitrogen gas.

p-Aminomethylstyrene (AMS) (1 g) was dissolved in 1 ml of methanol, and 9 ml of distilled water was added further to the solution. The aqueous solution was adjusted at pH 7.0, by adding hydrochloric acid. The above EDM grafted capsules were put into this solution, and the graft polymerization was effected at 60° C. by adding potassium persulfate as initiator.

The results obtained are shown in Table 1.

TABLE 1

| No. | Number of capsules | Amount of AMS (g) | Amount of graft chain (μm) |
|---|---|---|---|
| 1 | 100 | 1 | 260 |
| 2 | 100 | 2 | 520 |
| 3 | 200 | 1 | 10.8 |
| 4 | 200 | 2 | 312 |

EXAMPLE 2

The grafted capsules prepared by No. 1 of Example 1 were put into 10 ml of 0.01M-phosphate buffer solution (PBS) of pH 7.2, and 0.5 ml of PBS solution containing 20 mM of glutaraldehyde (GA) dissolved therein was added to the solution containing the capsules. The solution was agitated for 3 hours at 37° C. After removing unreacted matters by washing, the same volume of PBS solution containing IgG dissolved therein was added to the capsules and the mixture was agitated at 37° C. for 3 hours to effect immobilization to the capsules.

Immobilization of human IgG was also effected using Woodward's reagent K (WR-K). Namely, 1 mg of WR-K reagent was dissolved in 10 ml of PBS solution, and the grafted capsules were put into the solution. Then, the solution was agitated at 5°-10° C. for 1 hour. After separation and washing, PBS solution containing human IgG dissolved therein was added to the capsules and agitation was effected at room temperature for 1 day.

The results obtained are shown in Table 2. By the way, although the amount of antibody was determined by weight, it was confirmed also by ELISA method.

TABLE 2

| | Amount of human IgG coupled (per 1 capsule) | | | |
|---|---|---|---|---|
| No. | Amount of capsules ($\mu g$) | Amount of WR-K (mg) | Amount of GA (mM) | Amount of antibody ($\mu g$) |
| 1 | 81.0 | 1 | | 125.8 |
| 2 | 81.0 | 1 | | 105.6 |
| 3 | 121.8 | 0.5 | | 64.0 |
| 4 | 121.8 | 1 | | 177.4 |
| 5 | 121.8 | 2 | | 205.4 |
| 6 | 130.2 | | 1 | 19.8 |
| 7 | 132.0 | | 1 | 21.1 |
| 8 | 135.0 | | 1 | 25.7 |

EXAMPLE 3

1. Preparation of human IgG immobilized capsule

IgG-immobilized, micrografted capsules were prepared according to the process of the above Example 2. The immobilization was effected using glutaraldehyde (GA) and WR-K reagent, in order to compare to differences in sensitivity among the processes for immobilization of IgG.

Then, PBS solution (10 ml) containing a fluorescent dye of 1-(quinamido-methyl)naphthalene (3 mg) dissolved therein was allowed to introduce the capsules by dialysis.

2. Determination of permeation coefficient

The human IgG immobilized, a micrografted capsule prepared in the above step 1 was added to 2 ml of anti-human IgG solution having a concentration as shown in Table 3 to allow to react at 37° C. for 15 mins, which was put in on optical cell, and the change in fluorescence at an excitation wave length of 280 nm and an emission wavelength of 340 nm was determined under agitation, using a fluorescent spectrophotometer (RF-540: Shimadzu Corp., Japan). The changes in permeation coefficient before the antigen-antibody reaction and 5 minutes after said reaction were determined according to the following equation:

$$\text{Permeation coefficient} = \frac{\text{Amount of dye released from capsules}}{\text{Amount of dye in total capsules}}$$

TABLE 3

| | Determined sensitivity of immobilized micrografted capsules | |
|---|---|---|
| IgG concentration (mg/ml) | Permeation coefficient (%) | |
| | GA method | WR-K method |
| $10^{-15}$ | 100 | 98 |
| $10^{-13}$ | 99 | 99 |
| $10^{-11}$ | 95 | 80 |
| $10^{-9}$ | 98 | 65 |
| $10^{-7}$ | 85 | 40 |

TABLE 3-continued

| | Determined sensitivity of immobilized micrografted capsules | |
|---|---|---|
| IgG concentration (mg/ml) | Permeation coefficient (%) | |
| | GA method | WR-K method |
| $10^{-5}$ | 70 | — |
| $10^{-3}$ | 55 | — |

EXAMPLE 4

Determination of protein A by a device using human IgG immobilized polymer film

Polyester cloth mesh (pore size: 33 $\mu m$, thickness: 72 $\mu m$) was allowed to adhere to one end of a polyethylene tube (inside diameter: 5 mm, outside diameter: 7 mm, length: 3 cm) while the circumference of said end was molten by means of a hot plate at approx. 160° C. Next, the mesh portion of the tube was impregnated with 0.2 ml of ethylenediamine and then dipped in a 1,10-bis (chlorocarbonyl)decane solution in a beaker. A nylon film is thus formed on the mesh of the tube, to form a liquor-pool. Then, grafting treatment and immobilizing treatment of IgG were effected on the external surface of the nylon film, in the same manner as Examples 1 and 2.

Determination of the change in permeation was effected by dipping the human IgG immobilized tube holding 0.2 ml of 1 mM-aqueous carboxyfluorescein solution beforehand introduced therein into a quartz cell in which a PBS solution containing protein A dissolved therein was taken. The results are shown in the following table:

| Concentration of protein ($\mu g$/ml) | Permeation coefficient (%) |
|---|---|
| 0 | 100 |
| 10 | 91 |
| 43 | 76 |
| 76 | 61 |
| 109 | 58 |

The agent or device of the present invention firmly immobilizes an antigen, antibody or hapten, and is capable of determining an antigen or antibody in a sample with a high sensitivity.

The immobilized method used in the present invention can be applied to immobilization of not only an antigen or anti-body but also an enzyme or the like, because it is possible to control the hydrophobism and hydrophilism of the surface of the capsule or the polymer film by properly selecting the monomer to be coupled to the capsule or the polymer film.

The process for determining antigen or antibody of the present invention is one which has never been tried in the art, in respect that the agent or device as described above is used and the change in releasing rate or released amount of dye is examined.

What is claimed is:

1. An agent for the determination of antigen or antibody which comprises a water-insoluble, dye-permeable polymer capsule having an average particle diameter of 0.1–5 mm, an antigen, antibody or hapten immobilized onto the surface of said polymer capsule through a polymer chain grafted to said capsule, and a hydrophillic dye solution enclosed in said capsule.

2. The agent of claim 1 in which the water-insoluble, dye-permeable polymer capsule is nylon capsule.

3. The agent of claim 1 in which the grafted polymer chain is one formed by the graft polymerization using a divinyl monomer and/or a vinyl monomer having a functional group.

4. The agent of claim 3 in which the vinyl monomer is p-aminomethylstyrene, ethyleneimine or allylamine.

5. A device for the determination of antigen or antibody, which comprises a liquor-pool composed, at least partially, of a water-insoluble, dye-permeable polymer film, an antigen, antibody or hapten immobilized onto the outer surface of said polymer film through a polymer chain grafted to said film, and a hydrophillic dye solution held in said liquor-pool.

6. The device of claim 5 in which the water-insoluble, dye-permeable polymer film is nylon film.

7. The device of claim 5 in which the grafted polymer chain is one formed by the graft polymerization using a divinyl monomer and/or a vinyl monomer having a functional group.

8. The device of claim 7 in which the vinyl monomer is p-aminomethylstyrene, ethyleneimine or allylamine.

9. The device of claim 5 in which the water-insoluble, dye-permeable polymer film is one formed on a porous or mesh substrate.

10. A method for determining antigen or antibody, which comprises subjecting the agent claimed in claim 1 or the device claimed in claim 5 into contact with a sample liquor to make the dye to release into the sample liquor, and determining the antigen or antibody in the sample liquor by detecting the change in releasing rate or released amount of the dye, which may be caused with the proceeding of an antigen-antibody reaction of the immobilized antigen, antibody or hapten, on the basis of the absorbance or fluorescence intensity.

11. The agent of claim 1, wherein the dye is a red, blue or fluorescent dye.

12. The agent of claim 11 wherein the dye is a red dye selected from the group consisting rhodamine, Bordeaux-S, fuchsine and eosine.

13. The agent of claim 11 wherein the dye is a blue dye selected from the group consisting of methylene blue and crystal violet.

14. The agent of claim 11 wherein the dye is a fluorescent dye selected from the group consisting of FITC, TRITC, XITC, carboxyfluorescein, and 1-(quinamidomethyl)naphthylene.

15. The agent of claim 5, wherein the dye is a red, blue or fluorescent dye.

16. The agent of claim 15, wherein the dye is a red dye selected from the group consisting rhodamine, Bordeaux-S, fuchsine and eosine.

17. The agent of claim 15, wherein the dye is a blue dye selected from the group consisting of methylene blue and crystal violet.

18. The agent of claim 15, wherein the dye is a fluorescent dye selected from the group consisting of FITC, TRITC, XITC, carboxyfluorescein, and 1-(quinamidomethyl)naphthylene.

19. The agent of claim 1, wherein said antigen, antibody or hapten immobilized on the surface of said polymer capsule couples to an antibody or antigen contained in a sample liquor such that the dye permeability of the polymer capsule is reduced.

20. The device of claim 5, wherein said antigen, antibody or hapten immobilized on the surface of said polymer film couples to an antibody or antigen contained in a sample liquor such that the dye permeability of the polymer film is reduced.

21. The method of claim 10, wherein the antigen-antibody reaction results in a decrease in the dye permeability of the polymer capsule or film.

* * * * *

UNITED STATES PATENT AND TRADEMARK OFFICE
CERTIFICATE OF CORRECTION

PATENT NO. : 5,081,048
DATED : January 14, 1992
INVENTOR(S) : Yoshio OKAHATA et al.

It is certified that error appears in the above-indentified patent and that said Letters Patent is hereby corrected as shown below:

Column 8

Claim 15, change "The agent" to --The device--

16, change "The agent" to --The device--

17, change "The agent" to --The device--

18, change "The agent" to --The device--

Signed and Sealed this

Twenty-second Day of November, 1994

Attest:

BRUCE LEHMAN

Attesting Officer

Commissioner of Patents and Trademarks